Figure 1:
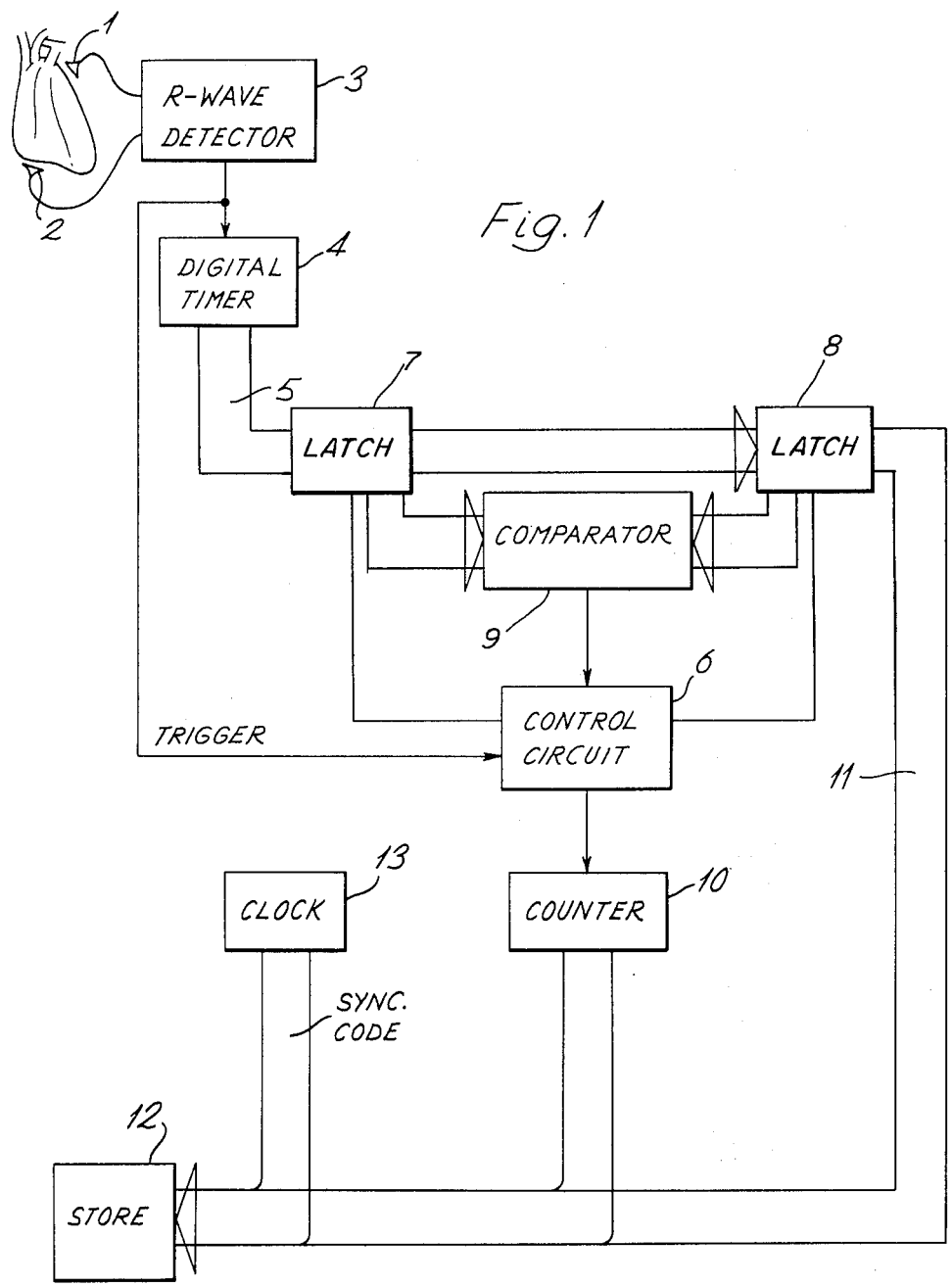

United States Patent [19]

Morris

[11] 4,346,718

[45] Aug. 31, 1982

[54] APPARATUS AND METHODS FOR RECORDING TIME INTERVALS

[75] Inventor: Julian R. W. Morris, Abingdon, England

[73] Assignee: Oxford Medical Systems Limited, Abingdon, England

[21] Appl. No.: 12,111

[22] Filed: Feb. 14, 1979

[30] Foreign Application Priority Data

Feb. 22, 1978 [GB] United Kingdom ............... 6964/78

[51] Int. Cl.³ .............................................. A61B 5/04
[52] U.S. Cl. ................................ 128/710; 346/33 ME
[58] Field of Search ............................ 128/670–671, 128/689–690, 702–706, 710; 235/92 CA, 92 T, 92 TF, 91 D; 364/417, 569; 346/33 ME

[56] References Cited

U.S. PATENT DOCUMENTS

| T926,014 | 9/1974 | Bonner | 128/702 |
| 4,090,505 | 5/1978 | Mortara | 128/702 |
| 4,096,854 | 6/1978 | Perica et al. | 128/690 |

FOREIGN PATENT DOCUMENTS 2746300  4/1979  Fed. Rep. of Germany ........ 235/92 CA

OTHER PUBLICATIONS

Haisty, W. K. et al., "Discriminant Analysis of RR Intervals: An Algorithm for On-Line Arrythmia Diagnosis," Comp. and Biomed. Res., vol. 5, No. 3, pp. 247–255, Jun. 1972.

Primary Examiner—Stephen C. Pellegrino
Assistant Examiner—Francis J. Jaworski
Attorney, Agent, or Firm—Larson and Taylor

[57] ABSTRACT

A time interval recorder stores the magnitude of time intervals between events, e.g. heartbeats, over a period. The data is stored as a sequence of pairs of numbers representing respectively the magnitude of a time interval and the number of successive occurrences of the same time interval. The recorder comprises a digital timer, a comparator, a counter and a digital store. The timer provides a digital indication of each successive time interval which is compared in the comparator with the immediately previous digital indication. If there is equality then the counter is incremented. If there is non-equality then the count is stored in the store together with the digital value of the previous time interval and the counter is then zeroed. The store may also store digital indicators of elapsed time in the same sequence of stored numbers.

15 Claims, 3 Drawing Figures

| STORED CODE (OCTAL) | MEANING |
|---|---|
| 00 00 | SYNC. CODE |
| 33 40 | BIN 27 32 BEATS |
| 32 35 | BIN 26 29 BEATS |
| 07 01 | BIN 7 1 BEAT |
| 46 01 | BIN 38 1 BEAT |
| 37 77 | BIN 31 63 BEATS (OVERFLOW) |
| 37 17 | BIN 31 15 BEATS |
| 27 07 | BIN 23 7 BEATS |
| 00 00 | SYNC. CODE |
| 30 77 | BIN 24 63 BEATS (OVERFLOW) |

70 b.p.m.

72 b.p.m.

61 b.p.m.

61 b.p.m 81 b.p.m.

79 b.p.m.

Fig. 2

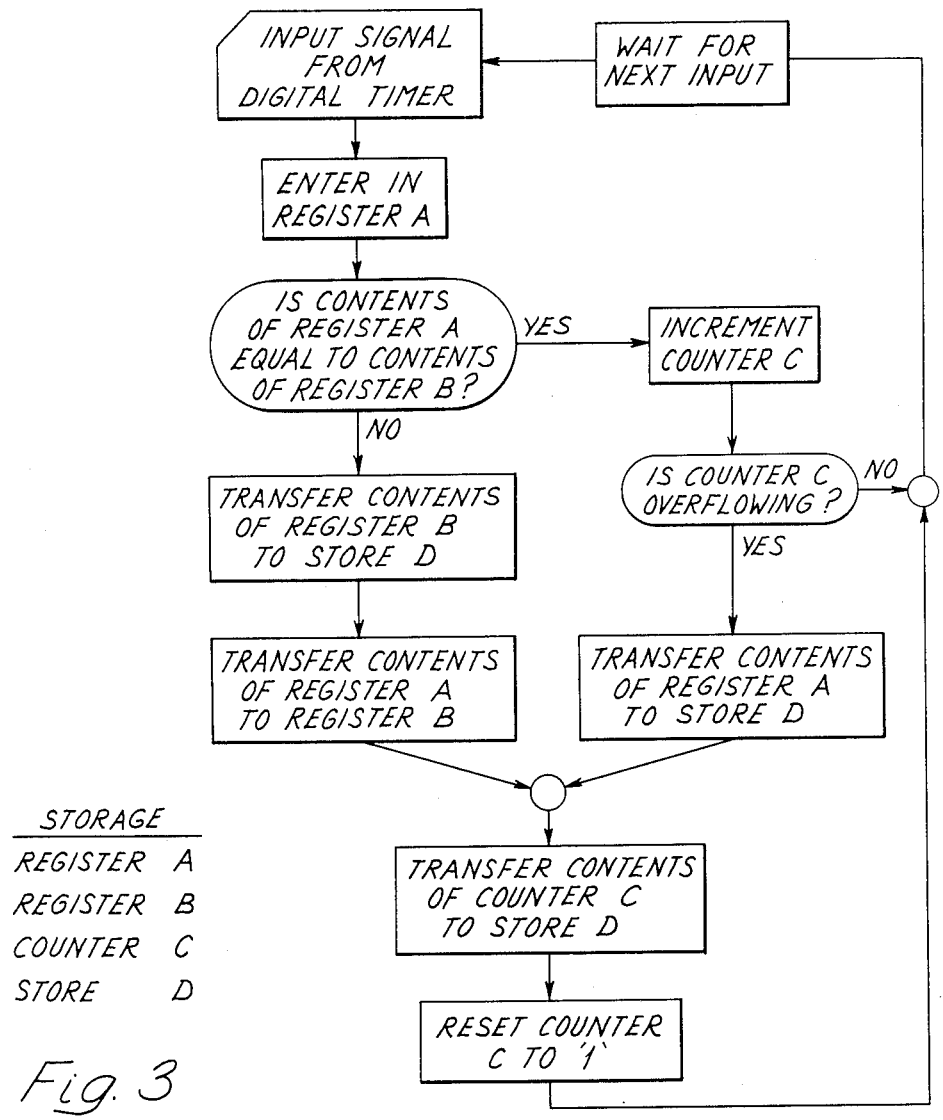
Fig. 3
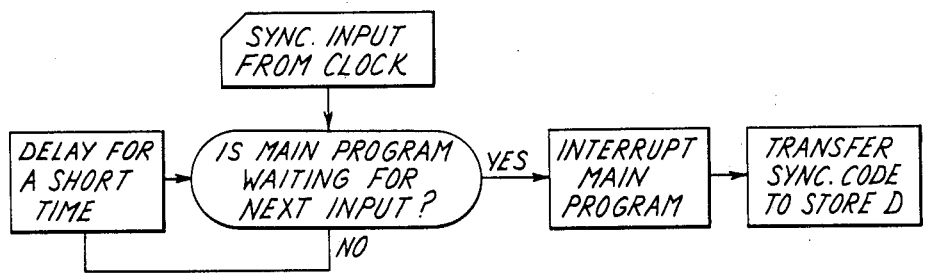

APPARATUS AND METHODS FOR RECORDING TIME INTERVALS

This invention relates to apparatus and methods for recording time intervals between repetitive events, particularly where such events occur rhythmically.

Such a requirement occurs for example in recording heartbeat rate, or more precisely the time interval between successive R-waves of an ECG waveform, termed the R—R interval. This interval is an important parameter in the diagnosis of heart malfunctioning especially if recorded over an extended period of several hours or even a whole day.

Equipment exists for monitoring ECG waveforms over an extended period utilising magnetic tape as the recording medium. While such equipment can be made compact enough for ambulatory monitoring it nevertheless requires a tape transport mechanism involving precision machining, skilled assembly and an electric motor which consumes a very large proportion of the power of a battery. Furthermore, the equipment makes audible noise and is prone to mechanical failure.

A solid digital storage does not have any of the above disadvantages and would allow for more rapid processing of the stored record. However, the size of memory required to store an ECG record of say a 24 hour period, as is readily possible with existing tape recorder equipment, would be prohibitive in respect of cost and size.

It is an object of the invention to provide for the storage of time interval information with a minimal demand on storage space.

According to the invention in one aspect apparatus for recording time intervals between repetitive events comprises means for measuring time intervals between successive such events, means for comparing the value of each succeeding time interval with the value of the previous time interval to indicate equality or non-equality to a predetermined degree of resolution, means for counting the number of successive indications of equality, and means for storing the said number together with the value of the previous time interval if non-equality is indicated.

Preferably the value of the previous time interval that is stored is stored as a digital representation. The means for storing thus stores pairs of numbers and these numbers can be stored in a single continuous sequence. Preferably also means are provided for converting the measured time intervals into digital representations before they are compared.

In carrying out the invention a counter may be provided for counting the number of successive indications of equality and the counter is incremented on each such successive indication. Conveniently the counter is reset after each recordal of the count therein. Elapsed time can also be recorded by storing time signals which are distinguishable from the other store of data in the same sequence at instants of time determined by a clock. The time signals may include real time information. According to the invention in another aspect a method of recording time intervals between repetitive events comprises the steps of measuring the time intervals between succesive such events, allocated a bin number to each measured time interval (which bin number is a number in a sequence of numbers and is indicative of the magnitude of the time interval), comparing each succeeded bin number with the bin number allocated immediately the previous thereto, generating an equality or non-equality signal as appropriate from said comparison step, counting the number of successive equality signals generated, and storing the count and associated therewith the immediately preceding bin number whenever a non-equality signal is generated.

In order that the invention may be more fully understood, reference will now be made to the accompanying drawings in which:

FIG. 1 illustrates apparatus embodying the invention in block diagrammatic form, FIG. 2 illustrates the stored information, and FIG. 3 is a flow chart.

Referring now to FIG. 1 there is shown therein time interval recording apparatus as applied to the recording of heartbeat rate. Suitable ECG waveform recording electrodes 1 and 2 are attached to a patient and the signals from these electrodes are taken to a detector 3 which provides a trigger pulse output coincident with each R-wave of the detected waveform, this being the most prominent spike in the waveform. The output from detector 3 is thus a train of pulses each of which occur at instants corresponding to an R-wave. The repetition rate of the pulses is thus the heartbeat rate.

The pulses from detector 3 are applied to a digital timer 4 which incorporates an internal clock pulse generator and a counter for counting the pulses from the generator. The arrival of a trigger pulse from detector 3 cause the transfer of the count present on the counter along a data highway path 5 and the resetting of the counter to zero. The time interval between successive trigger pulses is thus represented in digital form by the numbers transferred along highway 5.

Trigger pulses from detector 3 are also passed to a control circuit 6 which on receipt of a trigger pulse enters the digital information from highway 5 into a latch 7. A latch 8 holds the immediately preceding number.

The contents of latches 7 and 8 are then compared in a comparator 9 which generates either an equality signal if the numbers are equal, or else a non-equality signal if the numbers are different. The output from comparator 9, in the form of an equality signal or a non-equality signal as the case may be, is passed to control circuit 6. An equality signal causes a counter 10 to be incremented by one but initiates no other action. A non-equality signal from comparator 9 received by control circuit 6 causes the transfer of the contents of latch 8 along a data highway path 11 to a store 12, the incrementing of the count in counter 10 by one, and then the transfer of the count in counter 10 to store 12. Counter 10 is thereupon reset to zero and the contents of latch 7 transferred directly to latch 8.

It will be seen from the above that control circuit 6 has the inputs and the functions listed below. Each input causes the circuit to carry out the corresponding specific function or functions.

| Input | Function |
|---|---|
| Trigger pulse from detector 3 | Transfer date from timer to latch 7 |
| Equality signal from comparator 9 | Increment counter 10 |
| Non-equality signal from comparator 9 | Increment counter 10 |
| | Write contents of latch 8 and counter 10 in store 12 |
| | Reset counter 10 |
| | Transfer contents of latch 7 to latch 8 |

The sequence of events is as set out in the above table. A trigger signal from detector 3 initiates the sequence by causing transfer of data from timer 4 to latch 7 which overwrites the previous data that was held in latch 7. This transfer is automatically followed by an output signal from comparator 9 which will be either the equality signal or the non-equality signal. When an equality signal is generated control circuit 6 causes counter 10 to be incremented and there is no further action until the next trigger signal from detector 3 is generated. When a non-equality signal is generated then control circuit 6 carries out the functions of firstly incrementing counter 10, then writing the contents of latch 8 and counter 10 into store 12, then resetting counter 10 and then transferring the contents of latch 7 to latch 8 to overwrite the previous contents of latch 8. When these functions are carried out there is no further action until the next trigger signal is received from detector 3. Store 12 thus stores pairs of numbers, the numbers of a pair representing the magnitude of a time interval and the number of successive occurrences of the same time interval. These pairs of numbers are stored in a single continuous sequence in store 12.

If counter 10 overflows, an overflow signal is generated which writes the contents of latch 8 into store 12 followed by the maximum value of the count in counter 10. Counter 10 is then reset to zero. An independent clock 13 is also provided which at periodical intervals generates a unique digital code which is fed along highway 11 to store 12.

Choice of the pulse rate of the clock pulse generator included in timer 4 depends on the degree of resolution of the timing intervals that is desired. A high pulse rate increases the timing resolution but makes a greater demand on the storage space in store 12. The degree of resolution chosen can be considered as determining the width (in terms of time) of each of a series of "bins" into which successive time intervals are sorted in accordance with their magnitude. The bins are numbered consecutively so that a bin number is indicative of the magnitude of the time interval to which a bin is related.

The width of data highways 5 and 11 is chosen so that they can carry the total number of digits in the digital code representing the maximum number of bins that is available. This number represents the maximum time interval that timer 3 can measure.

The optimum size of counter 10 depends on the probability of the number of consecutive intervals likely to be in the same bin. Too large a counter would be wasteful of storage space in that store 12 must be arranged to be able to store the maximum count whenever this occurs. Too small a counter would also be wasteful in that it would generate too many overflows.

The output 10 and from latch 8 must be associated in some way in the store 12 for subsequent retrieval together. Store 12 can be organised to store the two numbers sequentially or else side by side. In the former case it is desirable that the two numbers have the same length in order to avoid wastage of storage space. In the latter case the numbers need not have the same length.

In operation of the apparatus a record of each time interval as represented by a bin number is not stored individually, but instead what is stored is the number of time intervals of equal digital value that occur consecutively together with a record of the associated bin number. This information is stored only when there is a change in bin number or a bin overflows. This results in a considerable saving in storage space.

FIG. 2 illustrates a typical sequence of numbers stored in store 12 together with an illustration of the information that they represent. The first column shows the numbers that are actually stored and these are indicated in an octal code. In the example illustrated there is space for only two octal digits in each number. This gives a maximum count in octal of '77' representing a possibility of sorting the time intervals into 63 different bins. As shown in FIG. 2 the bin number and the output from counter 10 are stored serially. Counter 10 thus also has a maximum count of octal '77' and is therefore set to generate an overflow signal on receipt of the sixty-third consecutive count.

The first item stored is a timing marker obtained from clock 13. This marker is generated on commencement and at every fifth minute and comprises a unique code represented by two sets of '00' digits. This will always be distinguished from a bin number or count, both of which have values in the range '01' to '77'. The next pair of code numbers stored is '33' and '40'. '33' in octal code indicates bin 27 and this bin represents a heartbeat rate of 70 beats per minute. The counter code '40' shows that there were 32 consecutive beats at that rate before the heartbeat rate speeded up slightly. When this change occurred a non-equality signal was generated by comparator 9 causing the contents of latch 8, which was octal code '33', together with the count then in counter 10, which was octal code '40', to be transferred to store 12. The new heartbeat rate was 72 beats per minute and the output from timer 4 was therefore a sequence of smaller numbers being octal code '32' representing bin 26. The number of beats at this rate was 29 before further change and counter 10 reached a count of octal '35' before a non-equality signal was produced in comparator 9 causing the codes '32' and '35' to be transferred to store 12.

The non-equality signal was due to the heart being monitored giving a premature beat and this was followed by an abnormally long pause. The time interval of the premature beat was such as to generate a code '07' from timer 4 while the pause generated a code '46'. This information was stored in store 12 with the count '01' being associated with each of the respective codes indicating that there were only single ones of each of the two time intervals.

The sequence of stored numbers also indicates the operation of the overflow signal. Following the premature beat and pause is a sequence of 78 at 61 beats per minute (bin 31 indicated by octal code '37'). However, counter 10 cannot hold a count of greater value than 63 (octal code '77') so that when 63 beats have been counted an overflow signal is produced which causes the bin number in latch 8, which is octal '37', to be written into store 12 followed by the maximum count of counter 10, which is octal '77'. Counter 10 is then reset to zero. The remaining beats at the same rate are then incremented in counter 10. The results in FIG. 2 show that there were another 15 such beats so that on the next subsequent change of beat rate the bin code '37' was again entered into store 12 followed by the count standing in counter 10, namely octal '17', representing the additional 15 beats. Were the measured heartbeat rate to remain constant over a long period a succession of such overflow signals would be recorded.

The storage process continues in the manner described above. FIG. 2 shows at the end a sequence of 7 beats at 81 beats per minute (bin 23 represented by octal code '27') and finally a sequence of 63 beats at 79 beats per minute (bin 24 respresented by octal code '30'). During the counting of this last sequence, clock 13 generates a signal showing that 5 minutes have elapsed measurements began. This signal is useful as a synchronising code and is stored in coded form as two sets of '00' digits. The generation and storage of the synchronising code does not interrupt the time interval measurement of the apparatus.

A two digit octal code requires 6 binary bits and assuming an average heartbeat rate of 70 beats per minute and a probable bin count of 32 before a change, then 12 binary bits are stored every 32 beats or every 27.4 seconds. Over a 24 hour period this gives a storage requirement of 37,839 bits which is well within the capacity of available single-chip solid stage serial memories.

While in the above described arrangement all the bins have equal widths, it is possible to interpose a digital translator in data highway 5 which will analgamate adjacent bins outside a range of particular interest and thus reduce the number of bins required to cover a given range of timing intervals, or more practically increase the range of timing intervals that can be measured at the expense of lower resolution outside a selected band.

The apparatus described above is arranged to measure heartbeat rate but it will be appreciated that such apparatus can also be used to measure other time intervals and will have particular advantage where there is a high probability that successive time intervals will be of similar magnitude.

While the invention has been described in connection with a hardware implementation, it will be understood that the various steps of comparison, counting and storing can be programmed for software implementation.

An example of a flow-chart or algorithm for enabling the invention to be carried out is shown in FIG. 3. A digital computing facility, which may be a general purpose computer or a microprocessor, is programmed to fulfil the requirements of the algorithm. The storage that is required for such a program is two temporary storage registers A and B, a counter C which filfils the function of the counter 10 in FIG. 1 and a store D equivalent to the store 12 in FIG. 1.

An input is obtained from the digital timer 4 in like manner to FIG. 1 and this input is then processed in accordance with the aglorithm. It will be seen that register A holds the present value of the input and register B holds the previous value thereof. The algorithm functions in a slightly different way to the operation of the apparatus shown in FIG. 1. The algorithm does not increment the counter when the comparison step indicates non-equality but instead the counter is reset to '1' and not zero. The algorithm can readily be modified to function as the FIG. 1 apparatus in this respect if desired. Likewise the FIG. 1 apparatus could be modified to operate in accordance with the steps of the algorithm. There is no significant difference in the two alternative modes of operation.

The programming of the output from clock 13 is also shown as a subsidiary algorithm. The clock generates a synchronising code which is transferred to store D in a manner which prevents interference with the execution of the main program.

I claim:

1. Apparatus for recording time intervals between repetitive events comprising means for measuring time intervals between successive such events, means for comparing the value of each succeeding time interval with the value of the previous time interval to indicate equality or non-equality to a predetermined degree of resolution, means for counting the number of successive indications of equality, and means for storing the said number together with the value of the previous time interval if non-equality is indicated.

2. Apparatus as claimed in claim 1 in which the value of the previous time interval is stored as a digital representation.

3. Apparatus as claimed in claim 1 in which means are provided for converting the measured time intervals into digital representations before they are compared.

4. Apparatus as claimed in claim 1 in which a counter is provided for counting the said number, which counter is incremented on each successive indication of equality and the means for storing records the number standing in the counter after each indication of inequality.

5. Apparatus as claimed in claim 4 in which the counter is reset after each recordal of the count therein.

6. Apparatus as claimed in claim 4 in which means are provided for storing the maximum count of the counter together with a digital representation of the magnitude of the time intervals then being counted and then resetting the counter when the counter overflows.

7. Apparatus as claimed in claim 1 in which means are provided for recording elapsed time in the store.

8. Apparatus as claimed in claim 7 in which the said means includes a clock and means for generating time signals distinguishable from other data signals at instants of time determined by the clock.

9. Apparatus as claimed in claim 8 in which the time signals are stored in a continuous sequence with the other data signals.

10. Apparatus as claimed in claim 1 and including means for detecting heart beats and providing a pulse train corresponding thereto for time interval measurement.

11. A method of recording time intervals between repetitive events comprising the steps of measuring the time intervals between successive such events, allocating a bin number to each measured time interval (which bin number is a number in a sequence of numbers and is indicative of the magnitude of the time interval), comparing each succeeding bin number with the bin number allocated immediately previous thereto, generating an equality or non-equality signal as appropriate from said comparison step, counting the number of successive equality signals generated, and storing the count and associated therewith the immediately preceding bin number whenever a non-equality signal is generated.

12. The method as claimed in claim 11 and including the step of resetting the count after each storing of the count.

13. The method as claimed in claim 11 and including the step of storing the count and the immediately preceding bin number when the count has reached a maximum count and then resetting the count.

14. The method as claimed in claim 11 in which the stored data is stored in a single continuous sequence.

15. The method as claimed in claim 14 and including storing digital signals indicative of elapsed time intervals in the same sequence with the other stored data.

* * * * *